(12) United States Patent
Steudler et al.

(10) Patent No.: US 11,851,693 B2
(45) Date of Patent: Dec. 26, 2023

(54) METHOD FOR THE BIOTECHNOLOGICAL PRODUCTION OF THE BLUE-GREEN FUNGUS PIGMENT XYLINDEIN

(71) Applicant: TECHNISCHE UNIVERSITAET DRESDEN, Dresden (DE)

(72) Inventors: Susanne Steudler, Dresden (DE); Stephanie Stange, Dresden (DE); Hubertus Delenk, Dresden (DE); Andre Wagenfuehr, Dresden (DE); Christof Zeeb, Dresden (DE); Thomas Walther, Dresden (DE)

(73) Assignee: TECHNISCHE UNIVERSITAET DRESDEN, Dresden (DE)

( * ) Notice: Subject to any disclaimer, the term of this patent is extended or adjusted under 35 U.S.C. 154(b) by 374 days.

(21) Appl. No.: 17/276,820

(22) PCT Filed: Nov. 4, 2019

(86) PCT No.: PCT/EP2019/080062
§ 371 (c)(1),
(2) Date: Mar. 16, 2021

(87) PCT Pub. No.: WO2020/094552
PCT Pub. Date: May 14, 2020

(65) Prior Publication Data
US 2021/0261994 A1    Aug. 26, 2021

(30) Foreign Application Priority Data
Nov. 8, 2018   (DE) ..................... 10 2018 127 946.9

(51) Int. Cl.
*C12P 17/18* (2006.01)
*C12N 1/14* (2006.01)
*C12R 1/645* (2006.01)

(52) U.S. Cl.
CPC ............ *C12P 17/181* (2013.01); *C12N 1/145* (2021.05); *C12R 2001/645* (2021.05)

(58) Field of Classification Search
None
See application file for complete search history.

(56) References Cited

U.S. PATENT DOCUMENTS

2017/0081540 A1    3/2017   Robinson et al.

FOREIGN PATENT DOCUMENTS

EP    1736053 A1    12/2006

OTHER PUBLICATIONS

Van Court ("Stimulating Production of Pigment-Type Secondary Metabolites from Soft Rotting Wood Decay Fungi ("Spalting" Fungi)", 109-124, Solid State Fermentation, Advances in Biochemical Engineering/Biotechnology 169, (2019) Editor T. Scheper, Springer, Cham Switzerland). (Year: 2019).*

(Continued)

*Primary Examiner* — Robert J Yamasaki
*Assistant Examiner* — Charles Zoltan Constantine
(74) *Attorney, Agent, or Firm* — Perry + Currier Inc.

(57) ABSTRACT

The invention relates to a method for the biotechnological production of the blue-green fungus pigment xylindein from fungus biomass in a bioreactor, the reactor contents being inoculated with biomass that is uncoloured.

The invention also relates to the use of uncoloured biomass of the fungus culture *Chlorociboria* sp. for inoculation in the biotechnological production of the blue-green fungus pigment xylindein.

8 Claims, 3 Drawing Sheets

(56) References Cited

OTHER PUBLICATIONS

Weber, G. L., et al. "A method to stimulate production of extracellular pigments from wood-degrading fungi using a water carrier." Current Research in Environmental & Applied Mycology 6.3 (2016): 218-230.

Robinson, Sara C., et al. "Method of extraction and resolubilisation of pigments from C hlorociboria aeruginosa and S cytalidium cuboideum, two prolific spalting fungi." Coloration Technology 130.3 (2014): 221-225.

Stange, Stephanie et al., Optimization of pigment formation by the wood-discoloring fungus *Chlorociboria aeruginascens*. Part 2: Pigment formation in the wood substrate, (with English translation) Holztechnologie, Vol. 59, 2018, pp. 47-54.

Stange, Stephanie et al., "Optimization of pigment formation from the wood-discoloring fungus *Chlorociboria aeruginascens*. Part 1: Biomass and pigment formation on agar and in liquid media", (with English translation) Holztechnologie, vol. 59, 2018, pp. 52-60.

Weber, Genevieve, et al. "Pigments extracted from the wood-staining fungi *Chlorociboria aeruginosa, Scytalidium cuboideum,* and *S. ganodermophthorum* show potential for use as textile dyes." Coloration Technology 130.6 (2014): 445-452.

Saikawa, Yoko, et al. "Absolute configuration and tautomeric structure ofxylindein, a blue-green pigment of *Chlorociboria* species." Phytochemistry 55.3 (2000): 237-240.

Robinson, Sara C., et al. "Potential for carrying dyes derived from spalting fungi in natural oils." Journal of Coatings Technology and Research 14.5 (2017): 1107-1113.

Robinson, Sara C., et al. "Stimulating growth and xylindein production of Chlorociboria aeruginascens in agar-based systems." AMB Express 1.2 (2012): 1-7.

Harrison, Robert, et al. "Fungi-derived pigments as sustainable organic (opto) electronic materials." Society of Photo-Optical Instrumentation Engineers (SPIE) Conference Series. vol. 10101. 2017.

Boonloed, Anukul, et al. "Centrifugal partition chromatography: A preparative tool for isolation and purification of xylindein from Chlorociboria aeruginosa." Journal of Chromatography A 1478 (2016): 19-25.

\* cited by examiner

METHOD FOR THE BIOTECHNOLOGICAL PRODUCTION OF THE BLUE-GREEN FUNGUS PIGMENT XYLINDEIN

CROSS-REFERENCE TO RELATED APPLICATIONS

This application is a continuation under 35 U.S.C. § 371 of International Application No. PCT/EP2019/080062 filed on Nov. 4, 2019 that claims priority to German National Application No. 10 2018 127 946.9 filed on Nov. 8, 2018, the entire contents of which is incorporated herein by reference.

The field of application of the invention is the biotechnological production of a fungus pigment which is usually used as a colourant.

Xylindein is a natural blue-green pigment (molecular formula $C_{32}H_{24}O_{10}$, CAS No. 3779-11-1), which is produced from fungi of the genus Chlorociboria sp., green wood cups, and has the following chemical structure:

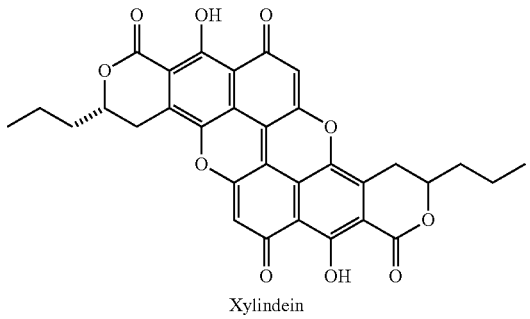 [SMILES: CCCC1Cc2c(c(O)c3c(=O)cc4oc5c6c(c(O)c7c(=O)cc8oc2c3c4c8c57)C(=O)O[C@@H](CCC)C6)C(=O)O1]

Xylindein

This pigment is known for the natural blue-green discolouration of wood. This wood, which is naturally discoloured in the forest, has been used for intarsia for several centuries. Xylindein is also promising for use as a fluorescent marker or as an organic semiconductor. There is currently no way to chemically synthesise xylindein.

Producing xylindein biotechnologically and isolating it from green-coloured cell culture supernatant and green-coloured cell biomass is known from the literature.

For example, Harrison et al. (2017) first cultivated the fungus Chlorociboria aeruginosa on malt-agarose plates in order to cultivate it on a 1 L scale after transfer of the biomass into a bioreactor.

Weber et al. (2016) examined the cultivation of various fungi, including Chlorociboria sp., in shake cultures. Xylindein was extracted from the cell culture supernatant there. Yields were not disclosed. The cultivation times are very long, however, at 48 d (7 weeks).

Stange et al. (2018, part 1) disclosed the cultivation of the fungus culture in food residues such as orange juice. Various substrates such as wood, coffee grounds, hay or rice were tested. It is also described that nutrient-limited conditions in the form of a lower nitrogen content in comparison with the available carbon concentration are favourable for the formation of xylindein. Different N sources and C sources were tested and mixed.

The hot water extraction of tree bark for producing a suitable cultivation medium, which contains secondary plant substances, is also described.

Robinson et al. (2014) applied the concept of extracting xylindein directly from the fungus biomass and coloured solid substrate, instead of producing it from the cell culture supernatant of a liquid cultivation. Robinson et al. also examined the solubility of xylindein in, i.a., acetonitrile, tetrahydrofuran or ethanol.

Saikawa et al. (2000) extracted from Chlorociboria sp. infested wood by means of hot chloroform.

Weber et al. (2014) described the extraction of xylindein from a Chlorociboria aeruginosa culture from malt agar plates consisting of 2% malt and 1.5% agar by means of dichloromethane.

Stange et al. (2018, part 2) used this concept and coloured solid wood by cultivating fungi in liquid media such as orange juice. The aim of the work was to find suitable types of wood as a substrate for this fungus cultivation. To this end, they developed a prototype-scale solid material reactor for targeted mycological wood discolouration.

In US2017/0081540A1, acetone, tetrahydrofuran and acetonitrile were used to extract fungus pigment from discoloured substrates. In a further step, the extract was mixed with an oil which, after evaporation of the solvent, acted as a liquid carrier for the fungus pigment. A suspension of the pigment in oil could thus be produced. This pigment suspension is intended to be used as a paint.

The extraction of pigments using hot water, both from infested wood and from fungal mycelium, is suggested in EP1736053A1. The purification method described is precipitation by acidification in combination with filtration.

In summary, it is clear from the prior art that a cultivation has hitherto only been implemented on a 1 L scale. The cultivation times described are very long. Said times are at least 6 weeks. The solvents used in the extraction are impractical for industrial use due to high toxicity and the associated necessary safety precautions.

The problem addressed by the invention is that of providing a method that allows shorter process times. The cultivation time should be low. The productivity of the fungus culture should be high.

Overall, just as much or more xylindein should be obtained in a shorter time than in known methods from the prior art. The method should be simple to carry out and ecological.

According to the invention, the problem is solved by the features of the independent claims.

Preferred embodiments of the invention are the subject matter of the respectively dependent claims.

The invention relates to a method for the biotechnological production of the blue-green fungus pigment xylindein in a bioreactor, comprising the steps of:
a. bringing the reactor contents into contact with biomass of the fungus culture Chlorociboria sp. and stirring the reactor contents to form xylindein-containing biomass,
b. separating the xylindein-containing biomass which formed in step a.,
c. extracting the xylindein from the biomass separated in step b. using a solvent, characterised in that the biomass with which contact is made in step a. is uncoloured biomass.

Steps a, b and c take place successively in this order.

"Bringing the reactor contents into contact with biomass of the fungus culture", in accordance with the invention, is understood as inoculation; i.e., a relatively small amount of fungus culture is added to the relatively large reactor contents in order to reproduce.

Chlorociboria sp., i.e. fungi from the genus Chlorociboria, is used as the fungus culture.

Said contact includes the reactor contents being brought into contact with isolated biomass of the fungus culture, for example in the form of a purified fungal mycelium, and the biomass being applied to a substrate, such as wood or agar infested with fungus culture, so as to adhere thereto.

Within the meaning of the invention, reactor contents means the contents of the bioreactor according to the invention, in particular the mostly liquid contents consisting of nutrient medium, additives, etc., for example.

Within the meaning of the invention, biomass is the substance mass of the fungus culture. What is referred to as fungal mycelium is in particular included.

The term "uncoloured biomass" in the context of the invention means biomass of the fungus culture, the metabolism of which is still configured in such a way that no or only very little blue-green fungus pigment xylindein is produced. The biomass is therefore uncoloured. In particular, it apparently has no blue-green colouration or no blue-green colouration which can be seen yet. It can also be referred to as light biomass.

It is also possible that the cell culture supernatant does not contain any xylindein, but the fungus biomass is already strongly blue-green coloured and therefore contains xylindein, in which case the term uncoloured biomass is no longer used.

The advantage of the invention is that the method allows a surprisingly short cultivation time, which leads to significantly shorter process times, and thus more xylindein per time can be produced than using conventional methods.

Within the meaning of the invention, process time is the time to produce a certain amount of xylindein using the method according to the invention, i.e. time per mass of xylindein. By bringing the reactor contents into contact (i.e. inoculating) with uncoloured biomass, the cultivation time (i.e. the duration of contact and stirring in step a.) is reduced by at least 33% in comparison with the use of coloured, (primarily blue-green) xylindein-containing biomass as inoculum. The cultivation time or the process time of the entire method, i.e. including any precultivation steps carried out beforehand, is in particular shortened.

Another advantage resulting from this relationship is that the productivity in the method according to the invention is higher than in conventional methods. Productivity is the mass of xylindein produced (i.e. manufactured) from the fungus culture per volume of reactor contents per time. In this case, it is assumed that the losses in step b. and c. of the method according to the invention are negligibly small, and the amount of xylindein produced is therefore always proportional to the amount of xylindein produced by the fungus culture.

Another advantage is that the method is wood-free, i.e. that no wood is required as a substrate for the fungus culture in the method.

It is also advantageous that the starting point of the production of the fungus pigment xylindein can be predicted on the basis of the curve of the pH of the reactor contents (FIG. 2). After a continuous increase in the pH during the cultivation of the uncoloured biomass according to the invention, the pH increase slows down and the pH finally briefly decreases. An increased xylindein production by the fungus culture begins at this change between the increase and decrease of the pH, and the blue-green colouration of the fungus culture becomes visible a short time later. Shortly before this change point, the nitrogen content is limited, which is the reason for the start of such a secondary metabolism.

An additional advantage of the method according to the invention is the storability and thus also the transportability of the intermediate product, i.e. the xylindein-containing biomass separated in step b. that can be dried. It is thus advantageously possible to carry out the method steps at different locations and to transport this intermediate product, preferably in dried form, for this purpose.

In one embodiment, uncoloured biomass is biomass which, after drying at 60° C., has an L value of ≥67, preferably ≥70 in the Lab colour space. Drying is in particular carried out at 60° C. for 24 hours.

In the Lab colour space, L=0 is defined as black and L=100 as white. In accordance with the typical blue-green colouration of the xylindein-containing biomass produced by *Chlorociboria* sp., the strength of the xylindein content in the biomass can therefore be determined by the L value (luminance=lightness) alone.

In a further embodiment, uncoloured biomass is biomass which is lighter than RAL 130 90 20 in the RAL colour system after the aforementioned drying. It is preferably lighter than RAL 130 90 10, particularly preferably lighter than RAL 140 90 05.

The invention also relates to the use of uncoloured biomass of the fungus culture *Chlorociboria* sp. for inoculation in the biotechnological production of the blue-green fungus pigment xylindein, in particular the use in the method according to the invention.

It can be assumed that there is a relationship between the composition of the nutrient medium, the metabolism of the fungal strain that is adapted thereto, and the metabolisation to xylindein or other colour-free metabolic products.

In this regard, in one embodiment the reactor contents comprise a nutrient medium. The nutrient medium preferably has a limitation of the available nitrogen in comparison with the total carbon content. The ratio of nitrogen source to carbon source in the nutrient medium is particularly preferably 1/400 (in the form of total nitrogen content to total carbon content, in each case in g). Under nitrogen-limited nutrient conditions, the fungus culture primarily forms xylindein, whereas, under nitrogen-rich nutrient conditions, uncoloured biomass is primarily produced.

In a preferred embodiment of the method according to the invention, the process parameters are controlled and regulated during step a. (bringing into contact . . . ).

This includes manual as well as automatic control and regulation.

In a preferred embodiment, the separation of the xylindein-containing biomass in step b. is a filtration. The filter material particularly preferably has a mesh size of at most 80 μm, in particular 80 μm. The filter material is in particular a material which is well suited for large volumes, such as a filter bag made of polypropylene woven fabric.

In a preferred embodiment of the method according to the invention, drying and/or comminution of the biomass takes place after the separation of the xylindein-containing biomass in step b. and before step c. The drying is particularly preferably carried out in combination with subsequent comminution, for example by grinding. This drying in particular takes place at a maximum of 70° C. and/or in a planar manner, with a maximum load of 350 g of moist biomass per dm². The drying time at 70° C. is preferably 24 hours.

The advantage of this embodiment is that the storability of the intermediate product, specifically the xylindein-containing biomass separated in step b., is increased. Said biomass is therefore also more transportable.

In one embodiment of the invention, the fungus culture is *Chlorociboria* sp., selected from *Chlorociboira aeruginascens* and *Chlorociboria aeruginosa*. In a preferred embodiment, the fungus culture is *Chlorociboira aeruginascens*, particularly preferably selected from the strains ATCC®

24028, ATCC® 24029, ATCC® 200365, ATCC® 200366 and IHIA39 (NCBI BioSample: SAMN06706673).

In a preferred embodiment of the method according to the invention, the method is preceded by at least one precultivation step, preferably in a nutrient medium as is preferably selected elsewhere. In these steps, a preculture is used and the fungus biomass is propagated.

In this embodiment, reference is therefore made to pre-cultivation/preculture and main cultivation/main culture. The precultivation and the transfer of the fungus biomass from smaller into larger scales is a known method from the prior art and is usually multi-stage, as shown, for example, in FIG. 3. In this case, it is necessary to transfer the fungus into the next larger scale during the exponential growth phase.

In this embodiment, inoculation using fungus biomass which is uncoloured preferably takes place in the main culture and in each precultivation step. In this case, the necessary cultivation time is advantageously shortened in each of these steps. This means that the biomass is kept at the stage in which it is still uncoloured and produces little or no xylindein. As is known, the fungus always first forms uncoloured, light biomass during reproduction.

In a variant of this embodiment, the precultivation takes place in a nitrogen-rich nutrient medium, such as a 50 vol. % orange juice agar, in particular at 20-22° C. Inoculation, i.e. bringing into contact with uncoloured fungus biomass in accordance with the invention, then preferably takes place in a nitrogen-poor medium, as described above.

The advantage of the method according to the invention is that the colour change from uncoloured biomass to coloured, xylindein-containing biomass can be recognised on the basis of the pH curve of the culture medium, i.e. of the reactor contents. After a continuous increase in the pH during the cultivation of the fungus culture, the pH increase slows down and the pH finally briefly decreases. Xylindein production by the fungus culture begins at this change between increase and decrease, and the blue-green colouration of the fungus culture becomes visible a short time later. In particular during the precultivation steps of the latter embodiment, the point in time of the colour change can thus advantageously be predicted. This is helpful to keep the fungus culture at the stage in which little or no xylindein is produced.

In a preferred variant of the above embodiment, the precultivation takes place first on poured, nutrient-rich agar plates which are inoculated with the fungus culture according to the invention and incubated at 20-22° C.

In one embodiment of the method according to the invention, the solvent in step c. is a non-halogenated solvent. Said solvent is preferably selected from acetone, 2-butanone or a mixture thereof.

In an advantageous embodiment, the reactor contents contain a nutrient medium which is suitable for keeping the fungus culture of the invention alive, i.e. the method according to the invention is a method in liquid culture. Depending on the composition of the nutrient medium, the fungus culture will adapt its metabolism and the metabolic products may be changed. The method according to the invention advantageously also functions using nutrient media which contain fruit juices, even if these fruit juices are already older than specified by the best-before date. In this case, it is important that the organic residues contain carbohydrates (preferably glucose, mannose, maltose or sucrose) and an organic nitrogen source (e.g. proteins, peptides, yeast extract).

In one embodiment, the reactor contents preferably comprise a nutrient medium (i.e. a culture solution) which contains up to 50 vol. % food residues. Furthermore, a nutrient medium is comprised that contains a 1-20 vol. % orange juice solution, preferably a 3-15 vol. %, in particular a 5-10 vol. %, particularly preferably a 5 vol. %, orange juice solution. A 100% orange juice solution is understood to be orange juice having a fruit content of 100 vol. %.

In this embodiment, it can be seen (when monitoring the pH in the liquid reactor contents) that the higher the concentration of the orange juice in the nutrient medium is at the start of the cultivation, the later the colour change, i.e. the start of or increase in xylindein production, takes place. It is assumed that the higher the concentration of orange juice in the nutrient medium, the longer it takes to reach the nitrogen-limited state as a trigger of the secondary metabolism.

In one embodiment of the method according to the invention, the xylindein obtained in step c. is purified by the steps of
d. drying the xylindein and redissolving it in a water-soluble organic solvent
e. precipitating purified xylindein by adding water to the mixture from step d.

The drying in step d. is preferably only a removal of the majority of the solvent, which can be carried out, for example, in a rotary evaporator. The redissolution preferably takes place in a small amount of solvent. The precipitation by adding water in step e. expediently takes place with an excess of water, preferably in a volume ratio of 1:10 (1 part of water-soluble organic solvent from step d. and 10 parts of water from step e.) The xylindein is particularly preferably filtered out as a solid after the precipitation in step e. This is in particular followed by washing using water and drying at approx. 103° C. for preferably 24 hours.

In a likewise advantageous embodiment, further xylindein is separated from the liquid culture supernatant remaining in step b. after separation of the biomass by known methods such as filtration together with subsequent ultrafiltration, preferably only ultrafiltration, and concentrated.

The ultrafiltration, preferably using a pore size s 10 kDa, concentrates, for example, dissolved xylindein, suspended xylindein and xylindein-containing mycelium particles, which can be further used in step c. of the method according to the invention.

In one embodiment of the method according to the invention, step a. and b. of the method according to the invention, preferably only step a., are carried out in a sterile manner, and the reactor contents are kept sterile. In this case, sparging with air is preferably also carried out in a sterile manner by means of a filter. In one embodiment, an oxygen limitation during step a. of the method according to the invention is excluded.

In one embodiment of the method according to the invention, the stirring takes place in step a. at a maximum stirring speed at the edge of the stirrer, i.e. tip speed (stirrer tip speed), of 0.52 m/s.

In one embodiment, the bioreactor has a volume of 70 L. The liquid reactor contents in this case preferably have a volume of 55 L.

In a preferred embodiment, the bioreactor, together with its contents, in particular the nutrient medium, is heat-sterilized by known methods before the contact in step a.

Table 1 shows values of the colour determination of the biomass by means of Lab colour space and on the basis of the RGB colour scale.

Table 2 shows exemplary cultivation parameters for producing a preculture of *Chlorociboria* sp. (in a plurality of precultivation steps) and the main culture in the biotechnological production of the blue-green fungus pigment xylindein.

Table 3 shows the results of an embodiment (inoculation with uncoloured biomass) and a comparative example from the literature (inoculation with coloured biomass). The shortening of the cultivation time and the higher productivity in the embodiment can be clearly seen.

Table 4 shows the comparison of the embodiment with a comparative example from the laboratory.

Figure 1:
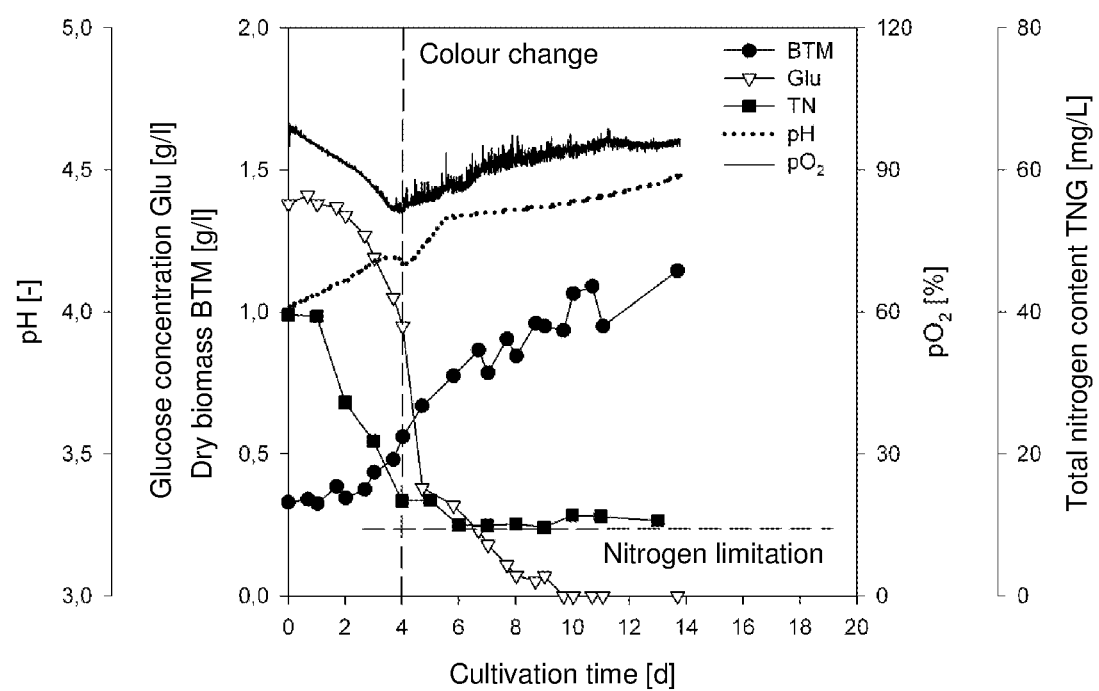
FIG. 1 shows the curve of numerous parameters, including the pH over the cultivation time, on the basis of an embodiment.
Figure 2:
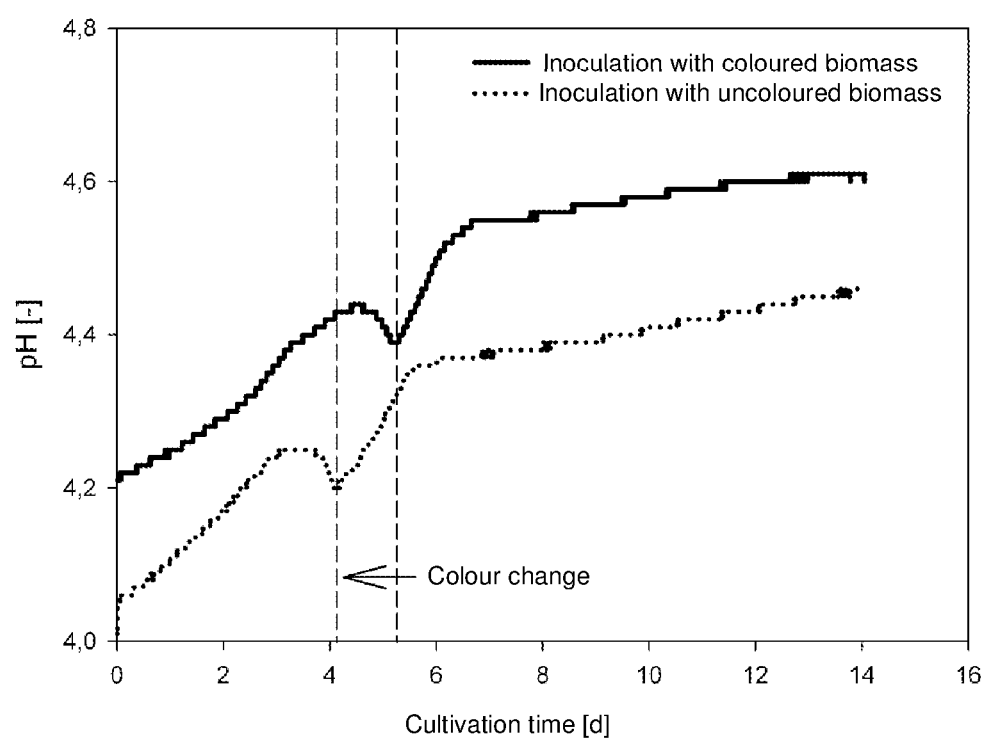
FIG. 2 shows the curve of the pH in the case of inoculation (of a main culture) with coloured or uncoloured fungus biomass, on the basis of an embodiment.
Figure 3:
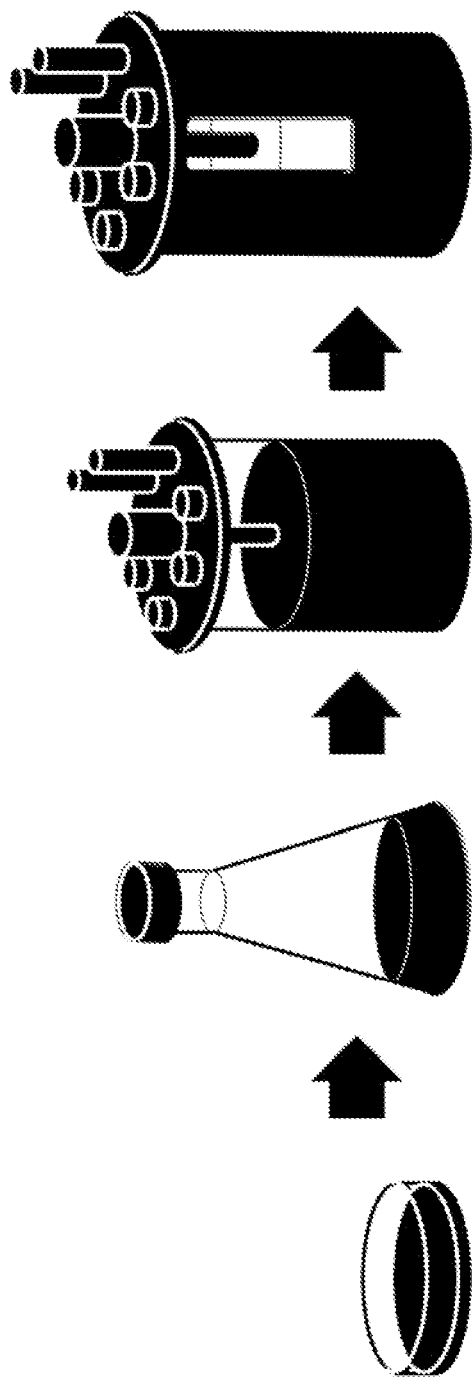
FIG. 3 shows, by way of example, the sequence of the method according to the invention in an embodiment, comprising precultivation (first, second and third part from the left-hand side) and main culture (right-hand part), inoculation (contact) with uncoloured biomass being carried out initially in each stage.

All embodiments of the invention can be combined with one another in any way.

EMBODIMENTS

The invention is illustrated by the following embodiments without being limited thereto.

Embodiment 1: Precultivation of the
Xylindein-Producing Fungus *Chlorociboria* sp.

The preculture for the process described in embodiment 1, step a. for producing blue-green fungus biomass took place in a plurality of cultivation steps. In this case, cultivation was initially carried out on a Petri dish scale in order to maintain the strain (maintenance of the fungus culture strain). A 50 vol. % orange juice agar consisting of 50 vol. % orange juice (100 vol. % orange juice is understood to be orange juice having a fruit content of 100 vol. %) and at least 30 g/L agar-agar (also referred to as agar, Chinese/Japanese gelatine or Japanese isinglass) was used for this purpose. The nutrient medium was autoclaved at 121° C. for 15 minutes. The poured agar plates were inoculated using an inoculation piece (plaque, 1 cm$^2$) of an older or acquired strain plate and incubated at 20-22° C. From this cultivation, two plaques were transferred into the shake flask scale and cultivated in an aqueous nutrient medium consisting of 5 vol. % orange juice. A total of 200 mL of precultivated fungus biomass suspension (preculture solution) was then transferred from the shake flask culture into a 3 L batch reactor (cultivation medium: 5 vol. % orange juice solution) and further cultivated. The pH was monitored continuously, and samples of the culture solution were taken regularly to determine the colour of the fungus biomass. It was cultivated until the increase in pH lessened and the pH began to decrease again. At the same time, the L value from the colour determination approached the limit at which a change from uncoloured to coloured biomass occurred. The cultivation of this preculture was stopped at L=85 (luminance value). Table 1 shows the values of the colour determination of the biomass by means of the Lab colour space and RGB colours. The method for determining the colour of the fungus biomass and the required pre-treatment is described in the following section.

During pre-cultivation, it is necessary to transfer the fungus into the next larger scale during the exponential growth phase. For this purpose, for the fungus *Chlorociboria aeruginascens* IHIA39, 7 days was determined for the shake flask culture and 7 days was also determined for the 5 L cultivation. This reduced the pre-cultivation time by at least 50% in comparison with the use of coloured, xylindein-containing biomass as inoculum.

Method for Determining the Colour of the Fungus Biomass

After a sample of the liquid culture was taken, the biomass contained was separated off by filtration, washed using distilled water and dried (directly on the filter paper) at 60° C. for 24 hours in a drying oven. On the basis of the dried biomass, the colour in the Lab colour space was determined by means of a spectrophotometer (Datacolor ELREPHO). The determined values are average values of 5 measured values. A conversion into, for example, RGB colours is possible using one of the available databases (for example http://www.cielab-farben.de/farbdatenbank.html).

TABLE 1

Determination of the colour of the biomass in different stages
Values are listed for uncoloured biomass (for inoculation), for biomass when the colour changes (from uncoloured biomass to coloured biomass) and for strongly blue-green coloured biomass.

|  | R | G | B | L | a | b |
|---|---|---|---|---|---|---|
| Inoculation | 215 | 212 | 194 | 85 | −1 | 9 |
| Colour change | 160 | 165 | 126 | 67 | −7 | 20 |
| Blue-green | 109 | 144 | 116 | 56 | −16 | 11 |
| colouration | 85 | 111 | 97 | 44 | −11 | 5 |

An L value (luminance = lightness) of approx. 70 was determined as the limit for distinguishing between coloured and uncoloured biomass.

Embodiment 1—Step a: Producing Blue-Green
Fungus Biomass on a 70 L Scale

For the main cultivation for producing blue-green fungus biomass containing xylindein, a 70 L bioreactor (Applikon Biotechnology B.V.) was supplied with 55 L of 5 vol. % orange juice in water. The nutrient medium was heat-sterilized at 123° C. for 30 min ("Sterilization in Place", SIP) in the bioreactor, and the process parameters (as listed in Table 2) were set. 5 L of preculture with uncoloured biomass (from embodiment 1, precultivation) were transferred to the reactor and cultivated for 14 days. By means of process monitoring, the point in time of the colour change of the fungus biomass from uncoloured to blue-green was determined by online measurement of the pH. During the cultivation, the pH increased from pH 4 to pH 4.2. From about day 4, the pH decreased slightly to 4.1 and increased again to pH 4.5 from day 5 to day 6. This pH behaviour indicates the colour change of the culture.

The cultivation parameters used are listed in Table 2.

TABLE 2 cultivation parameters of a preculture and the main culture of *Chlorociboria sp.* for the biotechnological production of the blue-green fungus pigment xylindein.

| | Production of the preculture | | | |
|---|---|---|---|---|
| Description | Precultivation step 1 in baffled flask | Precultivation step 2 in 3 L bioreactor | Precultivation step 3 in 7 L bioreactor | Main cultivation 70 L bioreactor |
| Volume | 500 mL | 3 L | 7 L | 70 L |
| Working volume | 200 mL | 2 L | 5.5 L | 55 L |

TABLE 2-continued cultivation parameters of a preculture and the main culture of *Chlorociboria sp.* for the biotechnological production of the blue-green fungus pigment xylindein.

|  | Production of the preculture | | | |
| --- | --- | --- | --- | --- |
| Description | Precultivation step 1 in baffled flask | Precultivation step 2 in 3 L bioreactor | Precultivation step 3 in 7 L bioreactor | Main cultivation 70 L bioreactor |
| H/D ratio | — | 1.5 | 1.8 | 2.2 |
| Stirrer type | Orbital | Disc stirrer | Disc stirrer | Disc stirrer |
| Number of stirrers | — | 2 | 3 | 3 |
| Stirrer diameter | — | 4.8 cm | 4.9 cm | 10 cm |
| Stirrer speed | 120 rpm | 150 rpm | 150 rpm | 100 rpm |
| Internal fittings | 3 baffles | 3 flow disrupters | 3 flow disrupters | 4 flow disrupters |
| Sparging type | Membrane | Ring sparger | Ring sparger | Ring sparger |
| Sparging rate | — | 0.5 vvm | 0.5 vvm | 0.27 vvm |
| Temperature control | Shaker | Rod/heating casing | Double casing | Double casing |
| Temperature | 22° C. | 22° C. | 22° C. | 22° C. |
| Inoculum | 2 × 1 cm$^2$ | 200 ml | 500 ml | 5 L |
| KLa value |  | 4.5 h$^{-1}$ | 7.9 h$^{-1}$ | 4.7 h$^{-1}$ |
| Tip speed |  | 0.38 m/s | 0.46 m/s | 0.52 m/s |
| Power requirement |  | 0.02 kW/m$^3$ | 0.04 kW/m$^3$ | 0.02 kW/m$^3$ |

TABLE 3 comparison of the results of the biotechnological production of the blue-green fungus pigment xylindein in the case of inoculation with coloured or uncoloured biomass

|  | Comparative example | Embodiment |
| --- | --- | --- |
| Inoculation with | Coloured biomass | Uncoloured biomass |
| Source | Literature (Boonloed et al. 2016). | Own research |
| Volume | 0.25 L | 55 L |
| Cultivation time (main culture) | 10 weeks | 2 weeks |
| Productivity | 3.5 mg/L/d | 4.8 mg/L/d |
| Amount of xylindein produced | 62 mg | 3.7 g |

The productivity indicates the amount of xylindein that was produced per litre of reactor contents per day. It is determined by weighing the xylindein produced in the method and dividing by the volume of the culture medium and the number of days of contact and stirring (step a.).

Accordingly, the yield is defined as the mass of xylindein produced divided by the volume of the reactor contents.

Comparative Example 1b—Inoculation with Coloured Biomass

All cultivations were also carried out in parallel using coloured, i.e. xylindein-containing biomass. These comparative examples were carried out analogously to the above regulations, with the difference that, after the first inoculation with the inoculation piece, it was only inoculated with coloured biomass.

TABLE 4 comparison of the results in the complete cultivation chain from the shake flask to the 70 L bioreactor.

|  | Comparative example | Embodiment |
| --- | --- | --- |
| Inoculation with | coloured biomass | uncoloured biomass |
| Source | Own research | Own research |
| Process time | 6 weeks | 4 weeks |
| Preculture (shake flask) | 2 weeks | 1 week |
| Preculture (7 L bioreactor) | 2 weeks | 1 week |
| Main culture (70 L bioreactor) | 2 weeks | 2 weeks |
| Onset of colouration of the main culture after | 6 d | 4 d |
| Absorption values of the supernatant of the main culture at 640 nm after the end of cultivation (correlated with the xylindein concentration) | 0.063 | 0.115 |

As can be seen in Table 4, as a result of the inoculation with uncoloured biomass, the process time of 6 weeks could be reduced by a third to 4 weeks, while the onset of colouration occurred more quickly at the same time. The absorption values of the supernatant at 640 nm after the end of cultivation (correlate with the xylindein concentration in the supernatant) show that more xylindein was produced when inoculating with uncoloured biomass than when inoculating with coloured biomass. This advantage is also evident with regard to the amount of xylindein contained in the fungus biomass.

Embodiment 1—Step b: Preparing the Xylindein-Containing Moist Biomass for Producing Blue-Green Xylindein-Containing Dry Biomass When the 70 L bioreactor was harvested, the blue-green, xylindein-containing moist biomass was separated from the liquid culture supernatant by filtration. A filter bag made of polypropylene woven fabric having a mesh size of 80 μm was used for this purpose. The liquid culture supernatant was also coloured blue-green. Xylindein diffused into the medium and residual, particularly small biomass particles were additionally produced from said liquid culture supernatant by means of ultrafiltration (10 kDa membrane).

The blue-green xylindein-containing moist biomass was dried at a maximum of 70° C. for 24 hours by drying in a planar manner on a metal sheet in an oven with a maximum load of 350 $g_{moist\ biomass}/dm^2$. The dried blue-green biomass was processed into powder (particle size<0.5 mm) in an ultracentrifugal mill.

Embodiment 1—Step c: Extracting the Xylindein

The powdered fungus biomass was mixed with the extraction agent 2-butanone (MEK). The blue-green fungus pigment xylindein dissolved in the extraction agent. The extract solution was separated from the extraction residue by filtration. The extractant was removed from the extract solution by rotary evaporation. The extract produced in this way was redissolved in 15 mL of solvent 2-butanone (MEK) and diluted with distilled water in a volume ratio of 1:10 (1 part MEK and 10 parts distilled water). The fungus pigment xylindein was precipitated and filtered out. The xylindein was then washed a plurality of times using distilled water and dried at 103° C. for 24 h.

LITERATURE

Stange, S., Steudler, S.; Delenk, H.; Werner, A.; Walther, T.; Bley, T.; Wagenführ, A.
*Optimierung der Pigmentbildung vom holzverfärbenden Pilz Chlorociboria aeruginascens, part 1: Biomasse—und Pigmentsbildung auf Agar und in Flüssigmedien Holztechnologie*, 2018, 59, 1, 52-60
Stange, S., Steudler, S.; Delenk, H.; Stange, R., Werner, A.; Walther, T.; Bley, T.; Wagenführ, A.
*Optimierung der Pigmentbildung des holzverfärbenden Pilzes Chlorociboria aeruginascens, Teil 1: Pigmentbildung im Holzsubstrat*
Holztechnologie, 2018, 59, 2, 47-54
Harrison, R.; Quinn, A.; Weber, G.; Johnson, B.; Rath, J.; Remcho, V.; Robinson, S.; Ostroverkhova, O.
*Fungi-derived pigments as sustainable organic (opto) electronic materials*
Proceedings of SPIE, 2017, 10101
Weber G. L.; Boonloed A.; Naas, KM.; Koesdjojo M. T.; Remcho V. T.; Robinson S. C.
*A method to stimulate production of extracellular pigments from wood-degrading fungi using a water carrier*
Curr. Res. Environm. Appl. Mycol., 2016, 6, 218-230
Weber, G.; Chen, H. L.; Hinsch, E.; Freitas, S.; Robinson S.
*Pigments extracted from the wood-staining fungi Chlorociboria aeruginosa, Scytalidium cuboideum, and S. ganodermophthorum show potential for use as textile dyes*
Color. Technol., 2014, 130, 445-452
Robinson, S. C.; Hinsch, E.; Weber, G.; Freitas, S.
*Method of extraction and resolubilization of pigments from Chlorociboria aeruginosa and Scytalidium cuboideum, two prolific spalting fungi*
Color. Technol., 2014, 130, 221-225
Boonleod, A.; Weber, G. L.; Ramzy, K. M.; Dias, V. R.; Remcho, V. T.
*Centrifugal partition chromatography: A preparative tool for isolation and purification of xylindein from Chlorociboria aeruginosa*
Journal of Chromatography A, 1478 (2016) 19-25
Saikawa, Y.; Watanabe, T.; Hashimoto, K.; Nakata, M.
*Absolute configuration* and *tautomeric structure of xylindein, a blue-green pigment of Chlorociboria species*
Phytochemistry 55 (2000) 237-240

We claim:

1. A method for the biotechnological production of the blue-green fungus pigment xylindein in a bioreactor, comprising the steps of
   (a) bringing the reactor contents into contact with a biomass of the fungus
      culture *Chlorociboria* sp. and stirring the reactor contents to form xylindein-containing biomass,
   (b) separating the xylindein-containing biomass which formed in step (a), and
   (c) extracting the xylindein from the biomass separated in step (b) using a solvent, wherein the biomass with which contact is made in step (a) is an uncoloured biomass.

2. The method according to claim 1, wherein the solvent in step (c) is selected from the group consisting of acetone, 2-butanone and a mixture thereof.

3. The method according to claim 1, wherein after the separation of the xylindein-containing biomass in step (b), dry and/or comminution of the biomass takes place and before step (c).

4. The method according to claim 1, wherein the reactor contents in step (a) comprise a nutrient medium which contains up to 50 vol % food residues.

5. The method according to claim 1, wherein the reactor contents in step (a) comprise a nutrient medium which contains a 1 vol % to 20 vol % orange juice solution.

6. The method according to claim 1, wherein the xylindein obtained in step (c) is purified by the additional steps of (d) drying the xylindein and redissolving it in a water-soluble organic solvent, and (e) precipitating purified xylindein by adding water to the mixture from step (d).

7. The method according to claim 1, wherein further xylindein is isolated by ultrafiltration of the liquid culture supernatant remaining in step (b) after separation of the biomass.

8. The method according to claim 1, wherein the fungus culture *Chlorociboria* sp. is selected from the group consisting of *Chlorociboria aeruginascens* and *Chlorociboria aeruginosa*.

* * * * *